United States Patent [19]
Kimmell, Jr.

[11] 3,952,747
[45] Apr. 27, 1976

[54] FILTER AND FILTER INSERTION INSTRUMENT

[76] Inventor: Garman O. Kimmell, Jr., 3125 N. Virginia, Oklahoma City, Okla. 73118

[22] Filed: Mar. 28, 1974

[21] Appl. No.: 455,582

[52] U.S. Cl. ............................ 128/303 R; 128/1 R; 128/214 F; 128/325; 128/348; 128/DIG. 11; 210/448
[51] Int. Cl.² ........................................ A61B 17/00
[58] Field of Search .................. 128/1 R, 127–130, 128/214 R, 243, 244, 260–264, 325, 344, 303 R, DIG. 6, DIG. 11, DIG. 16, 214; 210/437, 446, 448; 220/86

[56] References Cited
UNITED STATES PATENTS

| | | | |
|---|---|---|---|
| 2,281,448 | 4/1942 | Mathey | 210/448 |
| 3,334,629 | 8/1967 | Cohn | 128/325 |
| 3,546,431 | 4/1968 | Modin-Uddin | 128/1 R |
| 3,786,807 | 1/1974 | Dubin | 128/260 |

OTHER PUBLICATIONS

Fadali, et al. Surgery, Vol. 64, No. 3 Sept. 1968, pp. 634–639.
Klieman, Surgery, Vol. 68, No. 5, pp. 806–808, Nov. 1970.

*Primary Examiner*—Robert W. Michell
*Assistant Examiner*—Henry S. Layton
*Attorney, Agent, or Firm*—Laney, Dougherty, Hessin & Fish

[57] ABSTRACT

A filter for arresting the flow of a liquid entrained, deformable solid or semi-solid body through a tubular vessel or conduit, the filter including a plurality of convergent legs in generally conical array and joined at their convergent ends to an apical hub, each leg having a reversely bent hook at its end which is distal with respect to the hub. Each leg also includes a plurality of bends intermediate its length, which bends decrease the solids by-pass capability of the filter without concurrent fluid occlusion.

An intrument for inserting the filter in a tubular environment is provided and includes a carrier for supporting the filter in a collapsed, compact status, an ejector mounted in the carrier for ejecting or releasing the filter from the carrier and an elongated flexible tube connected to the carrier for moving the carrier and filter to the locus of use of the filter, and for supplying an ejector actuating fluid to the ejector.

19 Claims, 7 Drawing Figures

U.S. Patent  April 27, 1976  Sheet 1 of 2  3,952,747
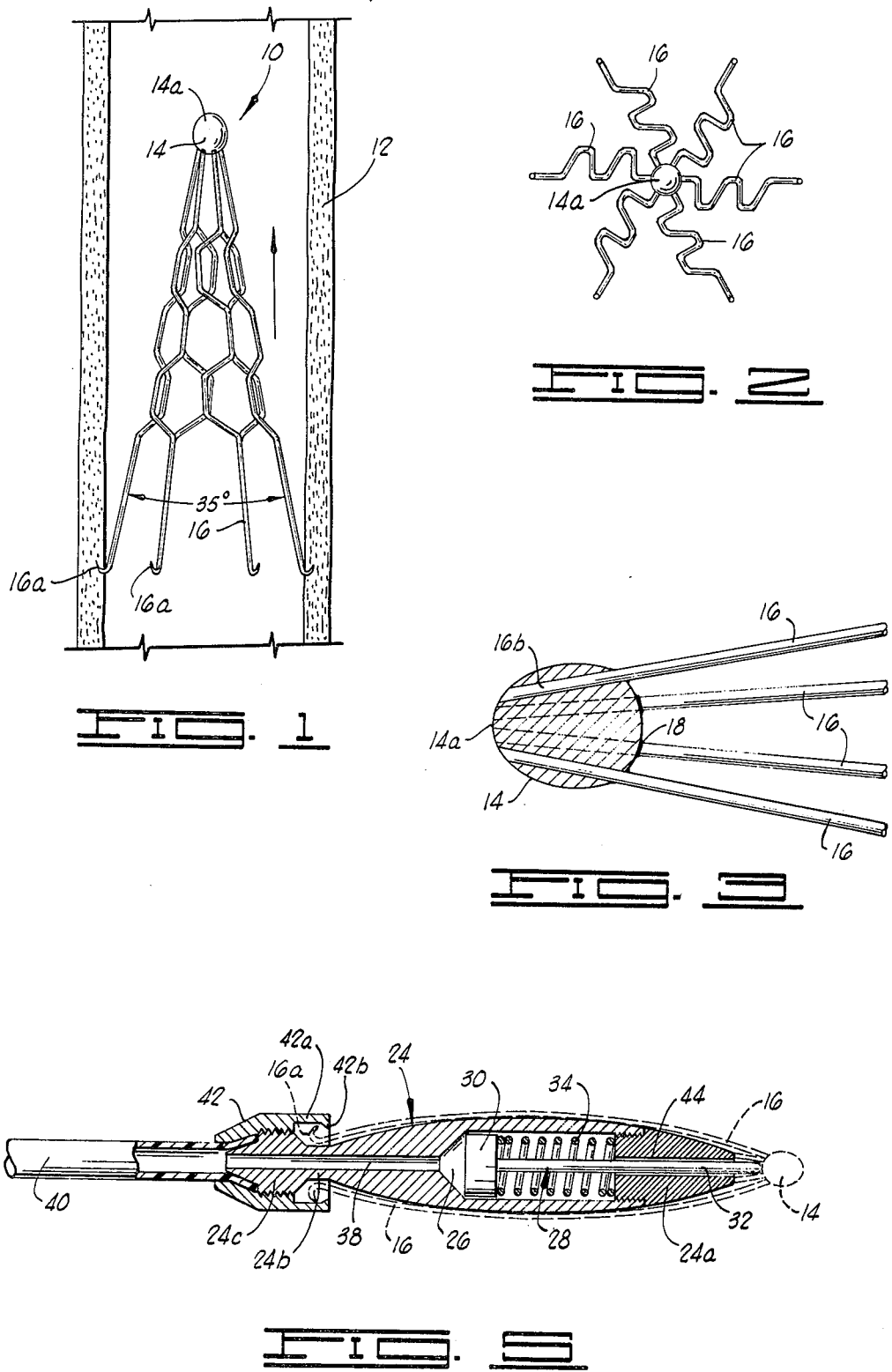

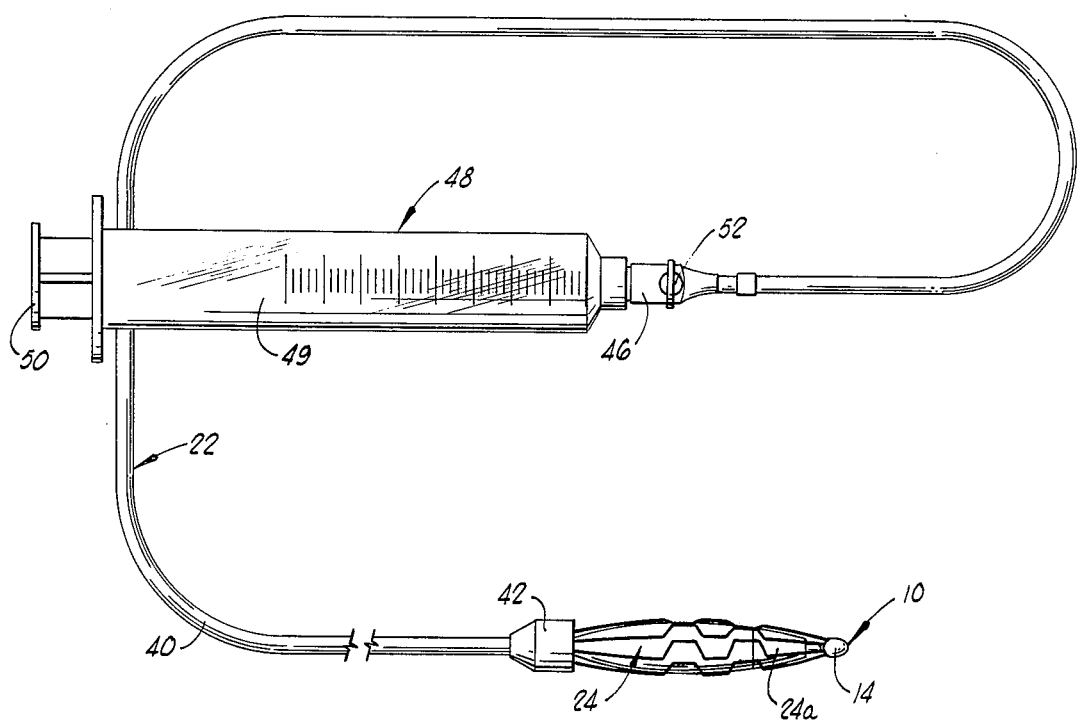
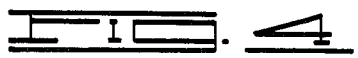
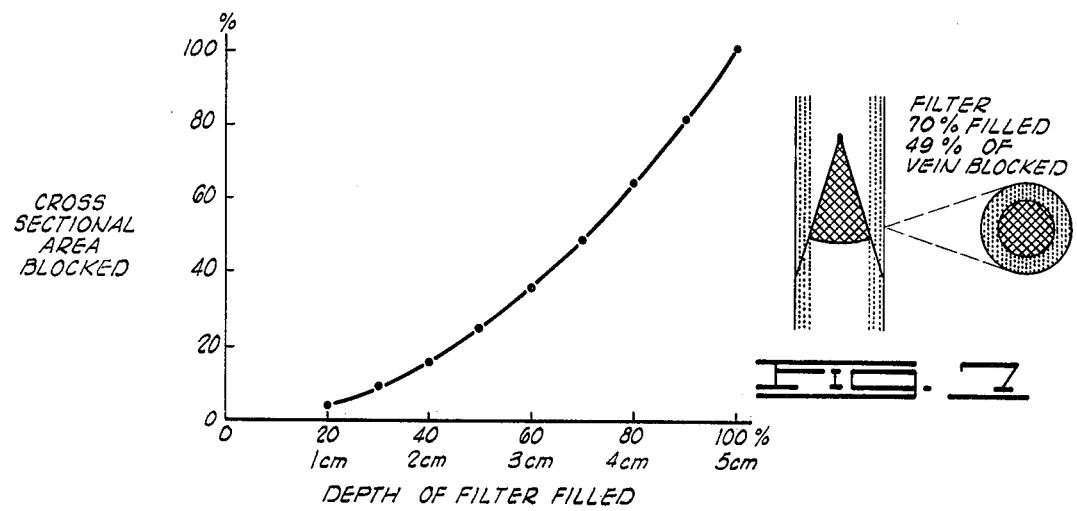
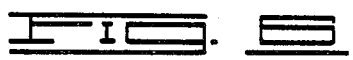

FILTER AND FILTER INSERTION INSTRUMENT

BACKGROUND OF THE INVENTION

1. Field of the Invention

This invention relates to filter devices, and more particularly, relates to devices especially, though not exclusively, useful for safely entrapping emboli moving in the circulatory system of animals.

2. Brief Description of the Prior Art

Blood clots (emboli) carried in the blood stream often constitute serious threats to health, and in some instances, to life itself, and the reduction of such clots, or their stabilization and arrest against further migration in the circulatory system of the body, are desiderata constantly motivating the development by the medical profession of new techniques for this purpose. Although emboli moving in other portions of the circulatory system can also present grave problems, techniques for preventing emboli from migrating into the pulmonary circulation from the vena cava have received an unusual amount of attention, since the development of this condition is relatively often experienced in post operative patients, and also may occur in phlebitic patients.

An early technique utilized involved ligation of the vena cava to arrest the movement of the embolus, with collateral circulation then being relied upon to provide adequate venal circulation to the heart. From this type of procedure, which involved a major abdominal operation requiring general anaesthesia and extensive surgery within the abdominal cavity, surgeons have progressed to the utilization of harpstring filters, staple plication, smooth, serrated, and channeling external clips, and even more recently, intravascular springs, balloons, and filters. The use of filters implaced in the vascular system provides the obvious advantage over ligation of major blood vessels, such as the vena cava, of not requiring general anaesthesia surgery and laparotomy. Other significant advantages of the filtering technique with respect to ligation will also be well understood by medically trained persons.

A recent proposal in the field of intravascular filters for entrapment and arresting of emboli is that which has been advanced by Mobin-Uddin and associates, and which is described in U.S. Pat. No. 3,540,431. The Mobin-Uddin filter is an umbrella type structure which includes a plurality of expanding struts or ribs carrying points at the divergent ends thereof which impale or engage the walls of the vena cava or other blood vessel when the filter is positioned at the desired location and permitted to expand to its operative state. In the Mobin-Uddin filter, the apex or hub of the device is located upstream from the pointed, divergent ends of the filter, and on occasion it has been found that the points on the struts of the filter do not adequately impale the internal walls of the vena cava. As a result, the filter becomes dislodged with highly dangerous migration and misplacement of the filter into other veins, as well as the occurrence of duodenal and ureteral perforation by the sharp points at the divergent ends of the filter struts. Further, the manner in which the filter is expanded and its orientation in the blood vessel may result in some perforation or penetration by the points at the ends of the filter struts completely through the blood vessel, with consequent undesirable internal hemorrhaging. The web or canopy extending between the struts of the filter also sometimes, when functioning to arrest movement of emboli in the blood vessel, presents a greater occluding effect than is desirable.

A catheter mounted filter device developed by Eichelter and Schenk is reportedly advantageous in that it is removable from the vascular system after it has performed its function. This filter device, however, has large interstices which may allow the escape of a portion of the entrapped emboli, and thus allow pulmonary embolization.

Another device which is designed to provide occlusion of the vena cava is that which is described in Cohn U.S. Pat. No. 3,334,629. The Cohn occlusion device is emplaced in the vena cava in an opposite orientation from the direction of emplacement of the Mobin-Uddin filter. This device offers some advantage in terms of reduced dislodgment by reason of the carriage on the divergent vanes of the device of a series of inclined teeth which impale the walls of the vena cava, and tend to become more firmly seated in the vascular walls under the impress of blood pressure developed by the flow of blood through the vessel. The techniques and devices proposed for emplacement of the Cohn occlusion device are attended by difficulty and some danger. Moreover, the Cohn structure is normally thought of as an occlusive device in the sense that some collateral circulation is often required in order to adequately supply blood to the heart, particularly when the entrapped embolus is large.

Ideally, an intravascular filter for use in the entrapment and stabilization against further migration of emboli should not merely effectively entrap and filter the emboli, but should permit the preservation of adequate blood flow without the requirement for collateral circulation. The latter condition is usually accompanied by the formation of uncontrolled venous collaterals which are potential sources of recurrent embolization. The filter, of whatever type, should show no tendency to propagate thrombus, and should be susceptible to emplacement at a precise predetermined location without undue patient risk, and preferably under local anaesthesia. To the extent that the filter may permit or, in fact contribute to, fibrinolysis of the entrapped thrombi, it will afford a further advantage and beneficial effect over complete or partial occlusion through ligation, and the use of the types of filters or obstructive techniques previously suggested.

BRIEF DESCRIPTION OF THE PRESENT INVENTION

Although it is useful for many types of filtering functions entailing the removal of solid or semi-solid materials from a fluid moving through a cylindrical body, the filter of the present invention finds its greatest utility in surgical procedures in which the filter is emplaced in a blood vessel for the purpose of trapping emboli. In this usage, it has demonstrated several marked advantages over other types of intravascular filters previously employed for this purpose. Moreover, although the filter structurally resembles, in several respects, the obstructive device which is illustrated and described in Mathey U.S. Pat. No. 2,281,448, it nevertheless is structurally different in a way which is of substantial importance in its described medical usage.

Broadly described, the filter of the invention comprises a plurality of generally conically arrayed convergent legs each having an end joined to an apical hub, and the second end carrying a reversely bent hook. Each leg preferably has a plurality of generally U- shaped bends therein, with such bends lying generally in the conical figure defined by the straight or unbent portions of the collective legs. This geometric arrangement serves two valuable functions in the operation of the filter. The bends in the legs perform a blocking or occluding function with respect to the semi-solid embolus trapped by the filter, and also appear to have a directing effect on embolus movement within the filter. In the latter regard, it is believed that the legs tend to turn the emboli inwardly toward the central axis of the filter so that its peripheral edges are subjected to the washing and flowing effect of the blood moving around the embolus and through the legs of the filter. This in turn allows ultimate fibrinolysis of the clot so that all danger of dislodgment or escape from the filter is then obviated. The centering effect of the bent legs also, of course, prevents blockage of the peripheral portions of the blood vessel in which the filter is located so that occlusion by projecting or protruding portions of the embolus which might otherwise project out from the side of the filter is reduced or obviated.

The present invention also includes, in combination with the filter, and also as a novel sub-combination standing alone, a filter insertion instrument for inserting the filter in a blood vessel of the human body. The insertion instrument comprises a carrier for supporting the filter in a collapsed, compact status with its hooks sheathed, an ejector mounted in the carrier for ejecting the filter from the carrier, and an elongated, flexible tube connected to the carrier for advancing the carrier along the blood vessel to the point therein where the filter is to be ejected for permanent emplacement. The tube also functions to house the ejector actuating instrumentality, which in a preferred embodiment, is a liquid which hydraulically actuates the ejector. Where hydraulic actuation is used, a suitable pump means, such as a manually actuated syringe, is used to transmit hydraulic pressure to the ejector via the liquid.

In inserting and positioning the filter, the syringe, tube and carrier are first flushed with the hydraulic liquid to displace all entrapped air. Fluid communication between the syringe and the tubing is then terminated by a suitable valve, stop cock, pinch clamp or the like to prevent accidental premature ejection of the filter. The filter is then folded down around the body of the carrier with its hooks sheathed, and the apical hub at the forward (advanced) end of the carrier. The carrier with the filter mounted thereon is then advanced into a suitable blood vessel by pushing the tube thereinto, following appropriate venotomy, and employing fluoroscopy to indicate the carrier and filter location at all times. When the filter is at the location where it is to function for the entrapment of emboli, the plunger of the syringe is depressed to hydraulically actuate the ejector. This pushes the filter off of the carrier, allowing the legs to spring outwardly and assume their generally conical configuration. The hooks at the end of the several legs of the filter then bite into and impale the walls of the blood vessel without penetrating such walls.

In a preferred use of the filter in the vena cava of the human body, a femoral venotomy is carried out and the carrier with the filter positioned thereon is advanced up into the vena cava via the femoral vein.

An important object of the present invention is to provide an improved filter which can be easily and quickly implanted in a blood vessel in the human body without the need for surgical procedures requiring general anaesthesia.

Another object of the invention is to provide a filter which is effective in the entrapment and retention of emboli moving in the bloodstream in the human body.

An additional object of the invention is to provide a vena cava filter which can be quickly and easily positioned at a desired location in the vena cava by insertion without undue patient risk and under local anaesthesia, using the femoral vein as a point of introduction of the filter into the vascular system.

An additional object of the invention is to provide a filter which can be used effectively to trap and retain emboli moving in the bloodstream of animals and which is more effective than prior filters of this type in preventing the escape or passage of small parts of the emboli through the structural members of the filter.

A further object of the invention is to provide a filter of high capacity for entrapping and retaining in a blood vessel, large emboli without the resultant occlusion of a substantial or major portion of the blood vessel in which the filter is located.

A further object of the invention is to provide an intravascular filter which, due to its unique structure, enables the normal blood circulation to ultimately dissolve, in a relatively shorter time as compared to other similar types of filters, an entrapped embolus.

Yet another object of the present invention is to provide an insertion instrument which enables an intravascular filter of the type having a plurality of divergent legs to be quickly, safely and easily inserted in a blood vessel to a predetermined location therein.

Another object of the invention is to provide an improved method for the positioning of an emboli filter within blood vessels of the human body, and particularly at a selected location in the vena cava.

The foregoing objects and advantages of the invention, as well as other desirable aspects thereof, will become apparent from the following detailed description of the invention when such description is read in conjunction with the accompanying drawings which illustrate the invention.

BRIEF DESCRIPTION OF THE DRAWINGS

FIG. 1 is a side elevation view of a filter constructed in accordance with the invention, and showing the filter in position in a blood vessel, such as the vena cava, with the blood vessel depicted in section.

FIG. 2 is an end view of the filter as it appears looking toward the apical hub forming a part of the filter.

FIG. 3 is a sectional view through the center of the apical hub forming a part of the filter, and illustrating the manner in which the legs of the filter are positioned in the apical hub and are retained therein.

FIG. 4 is a view in elevation of the filter mounted upon the carrier portion of a filter insertion instrument used for inserting the filter at a desired location in the body.

FIG. 5 is a longitudinal sectional view through the carrier forming a portion of the insertion instrument depicted in FIG. 4. The filter, as it is mounted on the carrier, is shown in dashed lines.

FIG. 6 is a graph illustrating the relationship of the depth to which the filter may be filled with an embolus (and thus its relative capture capacity), plotted against the cross-sectional area of the blood vessel which is blocked by the entrapment of an embolus filling the filter to a particular depth.

FIG. 7 is a schematic illustration of the relationship of filter capacity to the cross-sectional area of the blood vessel in which the filter is located.

DETAILED DESCRIPTION OF A PREFERRED EMBODIMENT OF THE INVENTION

A filter constructed in accordance with the invention is illustrated in FIG. 1 as it appears when it is in operative position within a large blood vessel, such as the vena cava. The filter is designated generally by reference numeral 10, and the wall of the blood vessel in which it is located is designated by reference numeral 12.

The filter 10 includes an apical hub 14 of overall egg-shaped or tear drop configuration and which has a generally hemispherically shaped end portion 14a. This construction avoids impalement of the filter on the blood vessel walls during emplacement, and also avoids irritation or scratching of the blood vessel during insertion of the filter. The apical hub 14 is drilled for the reception of the end portions of a plurality of legs as hereinafter described.

The filter 10 includes a plurality of elongated legs 16 which are of equal length and are identically configured to each other. The legs 16 are collectively arrayed in a conical geometric configuration so that the legs converge to the apical hub 14, and are symmetrically spaced about a central axis extending through the hub. Each of the legs is of equal diameter over its entire length and is made of a relatively resilient material, such as tempered stainless steel wire or the like. The legs may be coated with a polymeric, synthetic resin material having anti-thrombogenic properties. In the embodiment of the filter illustrated, six of the legs 16 are provided, and since each of these legs is identical to every other leg, only one of the legs will be described in greater detail.

At its outer end, or end which is distally located with respect to the apical hub 14, each leg is reversely bent through an angle of more than 90°, and is tapered or sharpened to a point 16a. The reverse bend is outwardly in a direction away from the central axis of the conical figure. As depicted in FIG. 3, the end portions of the several legs 16 project into bores formed through the apical hub 14, and are secured in the hub by means of a suitable eutectic braze material 18. The preferred angle of divergence between two opposite legs 16 is 35° at a time when the legs are in their relaxed, fully distended state, and this angle illustrated for the legs in FIG. 1 is substantially less due to the forced convergence of the legs at their outer ends by confinement within the walls of the blood vessel 12.

An intermediate portion of each of the legs 16 between the opposite ends thereof is bent through at least one, and preferably a plurality, of U-shaped bends. Each bend in the leg at this point is preferably such as to define an angle of from about 90° to 150°, with 120° being the most preferred angulation of each of the bends. The bends are made in a direction such that the portion of each leg bent from a straight line drawn between ends of the leg lies substantially in an imaginary surface formed by interconnecting the several legs to form an imaginary conical figure. It will also be noted that the bends of the legs are aligned with each other around the filter, and are all bent in the same direction with respect to the line in which the straight, unbent portions of each wire lie.

It will be seen in FIG. 1 that when the filter 10 is positioned in the blood vessel, the points 16a at the divergent ends of the legs 16 hook into or impale the wall 12 of the blood vessel, but the hooks are not of sufficient size to penetrate or pass through the wall of the blood vessel. It will further be noted by reference to the arrow within the blood vessel in FIG. 1 that when the blood flows in the direction indicated by the arrow, the pressure exerted by the blood on the filter 10, and any embolus which may be entrapped thereby, tends to set the hooks at the divergent ends of the legs 16 into the wall 12 of the blood vessel so that dislodgment of the filter is resisted.

The insertion instrument utilized for positioning the filter 10 at the desired location within the blood vessel is illustrated in FIGS. 4 and 5. The insertion instrument, designated generally by reference numeral 22, includes a carrier 24 having a parabolic or bullet-shaped body 24a which is of relatively large diameter at the center and tapers to relatively small diameter end portions. The carrier body 24a has a large cavity or chamber 26 formed in the enlarged central portion thereof for the reception of an ejector assembly designated generally by reference numeral 28.

The ejector assembly 28 includes a piston 30 of substantially the same diameter as the chamber 26, and an elongated ejector shaft 32. A helical compression spring 34 is positioned around the ejector shaft 32, and has one of its ends bearing against one end of the chamber 26 and its other end bearing against the piston 30. The chamber 26 communicates with an elongated bore 38 extending axially in the carrier body 24a and projecting through a neck portion 24b of the carrier which joins an externally threaded connector 24c to the bullet shaped portion of the carrier body. The externally threaded connector 24c has a frusto-conical portion through which the bore 38 extends, and one end of an elongated, flexible tubular member or catheter 40 is flared outwardly and pressed over the frusto-conical portion of the connector 24c as illustrated in FIG. 5. The end portion of the catheter 40 is retained in this position by means of a locking collar 42 which threadedly engages the connector 24c and includes a hollow, frusto-conical end portion which clamps the end portion of the tubing against the connector. The locking collar 42 includes an annular flange 42a which projects around, and is spaced radially from, the neck portion 24b of the carrier 24, and which carries an internal annular ramp 42b. The ejector shaft 32 extends from the chamber 26 through an elongated bore 44 disposed on the opposite side of the chamber from the bore 38 and communicating with the chamber.

The elongated tubular member or catheter 40 is secured at its end opposite the carrier 24 to a connector 46 having an open and exposed female end adapted to receive the discharge tip of a syringe 48. The syringe 48 is of conventional construction and includes a cylindrical barrel 49 having a plunger reciprocably mounted therein. The connector 46 is preferably a type which includes as a part thereof, a stop cock 52 which can be utilized to close off the catheter 40 from communication with the syringe 48. The purpose of this closure will be subsequently explained.

Operation and Method of Utiliziation of the Filter of the Invention

In its broadest utility, the filter of the present invention may be placed in substantially any type of tubular member having a liquid flowing therethrough with entrained solids which are to be filtered from the liquid stream, provided only that such tubular member provides either an abutment or shoulder, or has a wall which can be penetrated by the sharpened hooks carried on the ends of the filter legs. The filter, of course, in terms of such broad usage, can be pushed into the tubular member in a variety of ways. In that employment for which the filter is best adapted, however, it is inserted in a blood vessel using the insertion instrument depicted in FIGS. 4 and 5. Accordingly, the manner of inserting and positioning the filter, using such instrument, will be hereinafter described, and the method of insertion will be further restricted to that employed in positioning the filter in the vena cava.

At the outset, the syringe 48, catheter 40 and carrier 24 are made ready by filling the syringe with a suitable hydraulic, pressure transferring liquid which is compatible with the body fluids. The liquid is first forced into the catheter by depression of the plunger 50 within the barrel 49 of the syringe 48 to eject liquid from the syringe and force it into the catheter and into the chamber 26 in the carrier body 24a. This is done, before the filter is mounted on the carrier, for the purpose of forcing any entrapped air out of the system, and filling the system entirely with liquid. When this has been accomplished, the stop cock 45 is closed so that, when the filter has been placed in a transport position on the carrier 24, it will not be inadvertently ejected and wrongly positioned within the body as a result of accidental discharge of liquid from the syringe into the catheter. How this might otherwise occur will become clearer as the description proceeds.

In mounting the filter 10 on the carrier 24 of the insertion instrument 22, the filter is first placed around the bullet-shaped carrier body 24a so that its legs surround the carrier body in their relaxed or divergent position, and the apical hub 14 is oriented in advance of the carrier body in axial alignment therewith. With the filter 10 so positioned, a looped ligature is placed around the outside of the legs 16 of the filter, and the legs are drawn into substantial parallelism at the central portion of the carrier body and into convergence at that end of the carrier body adjacent the locking collar 42. The hooks 16a on the ends of the legs 16 are then inserted beneath an axially extending, peripheral flange forming a part of the collar 42. The hooks are thus protected, and the legs are kept folded snugly about the bullet-shaped carrier body. The ligature is then released, and the filter is ready for insertion in the body. The internal ramp 42b on the flange 42a of the collar is inclined at an angle of approximately 45°, and resists any forward movement of the filter on the carrier body 24 during manipulation of the insertion instrument 22 in the blood vessel.

The discharge of liquid from the syringe 48 into the catheter 40 effectively forces the piston 30 toward the opposite end of the chamber 26 against the resilient pressure of the spring 34 and the resistance offered to forward movement of the filter hooks by the ramp 42b. As the piston 30 moves across the chamber 26, the ejector shaft 32 is reciprocated in the bore 44 and impacts against the apical hub 14. As the ejector shaft 32 continues to be extended from the carrier 24, the filter 10 is forced along the carrier body to a point where the hooks 16a pass free of the ramp 42b carried by the collar 42 and the legs 16 can spring outwardly to their divergent, relaxed positions.

In the case of placement of the filter in the vena cava, a venotomy is performed on the femoral vein, since this provides the shortest route to the point of placement in the vena cava and avoids the necessity of passing the carrier, filter and catheter by the right atrium of the heart. The carrier is inserted into the vein with the hemispherically shaped nose portion of the apical hub in advance. The advance of the carrier 24 and the filter 10 is then effected by pushing or leading the catheter 40 into the vein. The progress of the carrier and filter are followed by fluoroscopy, and the position of final emplacement usually selected will be slightly below the level of the junction of the renal vein with the vena cava — usually at the second or third lumbar vertebra.

When the fluoroscopic examination indicates that the filter is positioned in the vena cava at the point where it is desired to permanently locate it, hydraulic pressure is developed by means of the syringe 48, and the filter is ejected from the carrier 24 in the manner hereinbefore described. The legs 16 of the filter then spring outwardly and, before reaching their most divergent, relaxed position, are arrested from further movement by contact of the sharpened hooks 16a with the wall of the vena cava. The hooks then impale the wall of the vena cava and are set by the spring action of the legs 16. It will be noted in FIG. 1 that the hooks 16a penetrate the wall 12 of the vena cava only a short distance, and that there is little danger of perforation of the wall by the hooks. With the filter released and in the described position, the catheter 40 is withdrawn, pulling with it the carrier 24. In this regard, it will be noted that the frusto-conically tapered outer surface of the trailing portion of the locking collar 42 will not scratch or damage the walls of the blood vessels through which it must pass during the retractive recovery of the carrier.

When the filter 10 is positioned in the vena cava in the position illustrated in FIG. 1, it is then able to perform its function of entrapping, retaining and ultimately facilitating the reduction of emboli moving in the bloodstream. The entrapment action entails, initially, movement into the flared, widely opened upstream end of the filter by the embolus, followed by a lodgement of the embolus in the downstream narrow end of the filter adjacent the apical hub 14. The bent configuration of the several legs aids in this placement of the embolus, since the U-shaped bends in the legs, configured as depicted in FIG. 1, tend to direct the semi-solid material making up the embolus inwardly toward the axis of the filter. Further, the bends in the legs of the filter also function to prevent passage of the material of the embolus, or any part thereof, between the legs so as to escape around the filter and continue downstream flow within the blood vessel. The bends effectively reduce the spacing between the legs so as to be more occlusive with respect to the embolic material, but this is accomplished without any significant restriction in freedom of blood flow between the legs of the filter.

As more of the embolus material enters the upstream end of the filter and continues to be accumulated in the more restricted downstream end of the filter, the filter gradually fills in an upstream direction. An important aspect of the filter of the present invention is its ability to accommodate and entrap a relatively large embolus without then offering significant occlusion of the blood vessel in which it is located. This characteristic of the filter is best illustrated in FIGS. 6 and 7 from which it will be seen that the filter may be filled by embolus material to a very considerable depth without concurrently occluding more than 60 or 70 percent of the total cross-sectional area of the blood vessel in which it is located. As a result, in part at least, of the propensity of the filter to centralize or direct the clot material toward the axis of the filter, and to offer no impediment or occlusive effect to the free flow of blood between the legs of the filter, the filter has been found to demonstrate the property of enhancing or accelerating fibrinolysis of the entrapped thrombi.

From the foregoing description of the invention, it will have become apparent that the filters of the invention, as well as the insertion instrument and insertion techniques constituting other aspects of the invention, provide real and very significant advantages in certain types of filtering operations, and particularly, in the entrapment, retention and ultimate reduction of emboli moving in the bloodstream of animals. Although certain preferred embodiments of the filter, insertion instrument and insertion method have been herein described in order to illustrate the basic principles underlying the invention, it will be understood that various changes and innovations in the described structures and method steps can be effected without departure from such principles. Changes and innovations of this type are therefore deemed to be circumscribed by the spirit and scope of the present invention, except as the same may be necessarily limited by the appended claims or reasonable equivalents thereof.

What is claimed is:

1. A filter for filtering solid and semi-solid materials from a liquid moving axially in a tubular vessel, said filter comprising:
   an apical hub; and
   a plurality of divergent legs each secured at one of its ends to said hub and each having
      a reversely turned hook on its end distal with respect to said hub; and
      at least one generally U-shaped bend intermediate its ends.

2. A filter as defined in claim 1 wherein said apical hub is rounded on a side thereof opposite the side from which said legs extend to avoid irritation and defacement of the interior of the tubular vessel as the filter is moved hub-first to a position of final emplacement in the tubular vessel.

3. A filter as defined in claim 1 wherein each of said legs has at least two of said generally U-shaped bends intermediate its ends, and said U-shaped bends are spaced from each other, and together form a W configuration, each angulation of each leg which forms a part of the U-shaped bend defining an angle of from about 90° to about 150°.

4. A filter as defined in claim 1 wherein each of said legs is a resilient wire coated with a synthetic resin material.

5. A filter as defined in claim 1 wherein said legs are of equal length and symmetrically positioned about a central axis extending from said hub.

6. A filter as defined in claim 5 wherein each of said reversely turned hooks is turned in a direction away from said central axis.

7. A filter for filtering solid and semi-solid materials from a liquid moving axially in a cylindrical vessel, said filter comprising:
   at least six resilient wire legs of substantially equal length positioned in conical array symmetrically about a central axis, each of said legs having at least two spaced U-shaped bends intermediate the length thereof, with the two bends forming together the configuration of a letter W, that portion of each leg which is in, and forms, said bends, lying substantially in the conical figure formed by the collective legs; and
   a hub at the apex of the conical figure formed by the collective legs and having an end of each of the legs secured thereto.

8. An insertion instrument for positioning a filter in a blood vessel of the body, said instrument comprising:
   a hollow, bullet-shaped carrier body;
   a piston mounted in the hollow carrier body;
   an elongated ejector shaft projecting from the piston through the carrier body for ejecting from the carrier body, a filter mounted externally thereon;
   means resiliently resisting movement of the piston and ejector shaft relative to said carrier body;
   a tubular member connected to said bullet-shaped carrier body for conveying a fluid to the hollow interior of the body for actuating said piston against said means resiliently resisting said movement of the piston and ejector shaft relative to the carrier body; and
   means for injecting a fluid into said tubular member at the end thereof opposite the end connected to said bullet-shaped body.

9. A filter for filtering solid and semi-solid materials from a liquid moving axially in a tubular vessel, said filter comprising:
   an apical hub having a hemispherical external end surface to facilitate progressive axial movement of the filter along the interior of the vessel without premature arresting of the filter movement through hub engagement with the vessel; and
   a plurality of divergent resilient legs collectively positioned in conical array and having ends secured to the hub, said legs each having a pointed, hook-shaped end portion at its end opposite the ends secured to the hub, and each of said legs characterized in having a U-shaped bends between the ends thereof.

10. An insertion instrument for positioning a filter in a blood vessel in the body, said instrument comprising:
    a bullet-shaped carrier body;
    a neck portion secured to one end of the carrier body;
    an ejector assembly mounted in the carrier body for ejecting the filter from the carrier;
    ejector assembly actuating means connected to the carrier body;
    a threaded connector secured to the neck portion; and
    a locking collar detachably securing said ejector assembly actuating means to said threaded connector, said locking collar including an axially extending peripheral flange spaced from said neck portion.

11. An insertion instrument as defined in claim 10 and further characterized as including an annular ramp positioned around the inside of said axially extending flange and spaced radially outwardly from said neck portion.

12. An insertion instrument as defined in claim 10 wherein said carrier body is characterized in having a chamber positioned centrally therein and aligned, axially extending bores extending from opposite sides of said chamber to opposite ends of the carrier body, and wherein said ejector assembly is movably mounted in said chamber.

13. An insertion instrument for positioning a filter in a blood vessel of the body, said instrument comprising:
    a solid carrier for carrying the filter;
    an ejector assembly mounted in the carrier for ejecting the filter from the carrier;
    an elongated catheter having one of its ends connected to said carrier; and
    a syringe connected to the opposite end of said catheter from the end thereof connected to said carrier for injecting an ejector assembly actuating fluid into the catheter.

14. An insertion assembly as defined in claim 13 wherein said ejector assembly comprises:
    a piston movably mounted in said carrier and responsive to pressure developed by actuation of said syringe; and
    means connected to said piston and movable therewith for displacing a filter carried by said carrier.

15. Apparatus for entrapping emboli entrained in circulating blood, said apparatus comprising:
    a bullet-shaped carrier body having bore means extending therethrough from one end thereof to the other;
    a filter demountably carried on the carrier body, said filter comprising:
        a hub positioned ata at end of said carrier body in alignment with said bore means; and
        a plurality of resilient legs each having one end secured to said hub, said legs extending along said body in peripherally spaced relation therearound;
    collar means secured to said carrier body at the opposite end thereof from said hub and encircling the ends of said legs opposite the ends secured to the hub for sheathing the encircled ends of said legs and biasing the legs into a retracted, folded position along the body; and
    demounting means movably positioned in said bore means in the body for demounting said filter from the carrier body.

16. Apparatus as defined in claim 15 and further characterized as including:
    fluid conveying means connected to said carrier body for supplying fluid to said bore means; and
    means for injecting a fluid under pressure into said fluid conveying means.

17. Apparatus as defined in claim 16 wherein said fluid conveying means is an elongated, flexible catheter tube.

18. Apparatus as defined in claim 15 wherein said filter is further characterized in having a hook on the end of each of said legs and encircled by said collar means.

19. Apparatus as defined in claim 15 wherein said demounting means comprises:
    a piston movably mounted in said bore means; and
    a shaft secured to said piston and projecting through said bore means to a point adjacent said hub.

* * * * *

UNITED STATES PATENT OFFICE
CERTIFICATE OF CORRECTION

Patent No. 3,952,747   Dated April 27, 1976

Inventor(s) Garman O. Kimmell, Jr.

It is certified that error appears in the above-identified patent and that said Letters Patent are hereby corrected as shown below:

Column 11, line 30, change "ata at end" to "at one end"

Signed and Sealed this

Sixth Day of July 1976

[SEAL]

Attest:

RUTH C. MASON
Attesting Officer

C. MARSHALL DANN
Commissioner of Patents and Trademarks